(12) United States Patent
Akagi et al.

(10) Patent No.: US 9,278,062 B2
(45) Date of Patent: Mar. 8, 2016

(54) EYE DROPS

(75) Inventors: Teiko Akagi, Osaka (JP); Takayuki Miyano, Osaka (JP); Motoyoshi Inooka, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 52 days.

(21) Appl. No.: 13/498,826

(22) PCT Filed: Sep. 29, 2010

(86) PCT No.: PCT/JP2010/066898
§ 371 (c)(1),
(2), (4) Date: Jun. 8, 2012

(87) PCT Pub. No.: WO2011/040433
PCT Pub. Date: Apr. 7, 2011

(65) Prior Publication Data
US 2012/0269760 A1    Oct. 25, 2012

(30) Foreign Application Priority Data
Sep. 30, 2009   (JP) ............................... P2009-228661

(51) Int. Cl.
*A61K 9/08* (2006.01)
*A61K 47/32* (2006.01)
*A61K 9/00* (2006.01)
*A61K 47/10* (2006.01)

(52) U.S. Cl.
CPC ............... *A61K 9/0048* (2013.01); *A61K 9/08* (2013.01); *A61K 47/10* (2013.01); *A61K 47/32* (2013.01)

(58) Field of Classification Search
CPC ....... A61K 9/0048; A61K 9/08; A61K 47/10; A61K 47/32
See application file for complete search history.

(56) References Cited

U.S. PATENT DOCUMENTS

| | | | |
|---|---|---|---|
| 5,188,826 | A | 2/1993 | Chandrasekaran et al. |
| 5,458,873 | A | 10/1995 | Kawashima et al. |
| 6,147,081 | A | 11/2000 | Noyori et al. |
| 6,511,949 | B1 | 1/2003 | Nitta et al. |
| 2002/0010193 | A1 | 1/2002 | Doi et al. |
| 2004/0079766 | A1 | 4/2004 | Kokubo |
| 2007/0053861 | A1 | 3/2007 | Nakayama et al. |
| 2007/0197648 | A1* | 8/2007 | Inooka et al. ............ 514/563 |
| 2009/0142321 | A1 | 6/2009 | Matsui |
| 2010/0216741 | A1 | 8/2010 | Matsumura et al. |
| 2010/0239518 | A1 | 9/2010 | Matsumura et al. |
| 2010/0249062 | A1 | 9/2010 | Matsumura et al. |
| 2013/0244978 | A1* | 9/2013 | Matsumura et al. ......... 514/57 |

FOREIGN PATENT DOCUMENTS

| | | |
|---|---|---|
| CA | 2616531 A1 | 2/2007 |
| CN | 1074224 A | 7/1993 |
| CN | 1502321 * | 6/2004 |
| CN | 1895284 A | 1/2007 |
| CN | 100453086 C | 1/2009 |
| EP | 1016406 * | 10/2005 |
| GB | 2007091 A | 5/1979 |
| JP | S54-067021 A | 5/1979 |
| JP | H2-503201 A | 10/1990 |
| JP | H5-247308 A | 9/1993 |
| JP | H11-130667 A | 5/1999 |
| JP | 2002-097129 A | 4/2002 |
| JP | 2002-201126 A | 7/2002 |
| JP | 2002-322048 A | 11/2002 |
| JP | 2003-055201 A | 2/2003 |
| JP | 2003-183157 A | 7/2003 |
| JP | 2004-123634 A | 4/2004 |
| JP | 2004-196417 A | 7/2004 |
| JP | 2005-008596 A | 1/2005 |
| JP | 2005-206599 * | 8/2005 |
| JP | 2005-343893 A | 12/2005 |
| JP | 2006-193521 A | 7/2006 |
| JP | 2006-219475 A | 8/2006 |
| JP | 2006-219476 A | 8/2006 |
| JP | 2006-219482 A | 8/2006 |
| JP | 2006-219484 A | 8/2006 |
| JP | 2009-502866 A | 1/2009 |
| JP | 2009-096790 A | 5/2009 |
| JP | 2009-132671 A | 6/2009 |
| JP | 2009-196903 A | 9/2009 |
| WO | 97/28827 A1 | 8/1997 |
| WO | 2005/025539 A1 | 3/2005 |
| WO | 2008/066644 A1 | 6/2008 |
| WO | 2009/035033 A1 | 3/2009 |
| WO | 2009/035034 A1 | 3/2009 |
| WO | 2009/041549 A1 | 4/2009 |

OTHER PUBLICATIONS

Machine translation of JP 2003-183157 (2003).*
English Machine Translation of CN1502321 2004.*
Office Action issued in counterpart Chinese Patent Application No. 201080042270.9 dated Mar. 13, 2013.
Extended European Search Report issued in counterpart European Patent Application No. 10820548.5 dated Feb. 3, 2014.

* cited by examiner

*Primary Examiner* — Mina Haghighatian
(74) *Attorney, Agent, or Firm* — Morgan, Lewis & Bockius LLP (57) ABSTRACT

An eye drop composition comprising a carboxyvinyl polymer and a monoterpene, and having a viscosity from 200 to 100,000 mPa·s. The monoterpene may be at least one selected from the group consisting of menthol, camphor and borneol. The carboxyvinyl polymer content may be from 0.001 to 10 w/v % with respect to the total volume of the eye drop composition, and the monoterpene content may be from 0.0001 to 1 w/v % with respect to the total volume of the eye drop composition.

2 Claims, 2 Drawing Sheets

EYE DROPS

The present application is a U.S. National Phase Application of International Application No. PCT/JP2010/066898 filed Sep. 29, 2010, which claims the benefit of priority of Japanese Application No. P2009-228661 filed Sep. 30, 2009, the disclosures of which are incorporated herein by reference in their entireties.

TECHNICAL FIELD

The present invention relates to an eye drop composition with good liquid drip, and to a method for improving the liquid drip of an eye drop composition.

BACKGROUND ART

High-viscosity ophthalmic compositions are useful for lengthening the residence times of compositions on the ocular surface thereby providing a sustained drug effect and preventing dry eye. Known thickening agents that are added to such high-viscosity ophthalmic compositions include cellulose-based polymers such as hypromellose, hydroxyethylcellulose and methylcellulose and vinyl-based polymers such as polyvinylpyrrolidone and polyvinyl alcohol and acrylic acid polymers such as carboxyvinyl polymer. Of these, carboxyvinyl polymers have a higher thickening effect than cellulose-based polymers that are widely used as components of an eye drop composition, and allow viscosities of several thousand to several tens of thousands mPa·s to be achieved even when used in small amounts, and they therefore serve as useful thickening agents.

Ophthalmic compositions such as an eye drop composition are generally housed and used in a container designed so that droplets can be dropped from an extraction opening (nozzle), by applying pressing force on the container. Modifications for dropping an eye drop composition from nozzles are therefore being devised.

For example, methods for improving liquid drip of an eye drop composition include the method described in Patent document 1 in which the material and shape of the nozzle are modified, but this method increases cost while also being limited to specific nozzle shapes, while it also places restrictions on the container shapes.

One method for dealing with poor liquid drip of an eye drop composition from nozzles is a method in which the nozzle is wiped with a clean wiper after each drip, in order to prevent deposition of the components, but this method not only fails to improve the liquid drip itself, but also increases inconvenience to the user. Also, Patent document 2 discloses a method of inhibiting deposition of components by addition of specific components into the liquid composition, but this method does not improve the liquid drip itself.

Addition of refrigerants such as menthol, camphor and borneol to ophthalmic compositions is already known. These refrigerants are known to impart a refreshing feel, while also exhibiting effects of alleviating ophthalmalgia induced by components (Patent document 3) and effects of improving the wettability of contact lenses (Patent document 4).

Addition of water-soluble polymers to ophthalmic compositions, in addition to refrigerants such as menthol, camphor and borneol, is also known. Such ophthalmic compositions are known to exhibit effects of improving the wettability of contact lenses (Patent documents 5 and 6), inhibiting adsorption of components onto contact lenses (Patent documents 7 and 8), maintaining a refreshing feel (Patent document 9), and alleviating irritation during drip (Patent document 10).

CITATION LIST

Patent Literature

Patent document 1: Japanese Unexamined Patent Application Publication No. 2004-196417
Patent document 2: Japanese Unexamined Patent Application Publication No. 2006-219484
Patent document 3: Japanese Unexamined Patent Application Publication No. 2002-201126
Patent document 4: Japanese Unexamined Patent Application Publication No. H11-130667
Patent document 5: Japanese Unexamined Patent Application Publication No. 2006-193521
Patent document 6: WO97/28827
Patent document 7: WO2005/025539
Patent document 8: Japanese Unexamined Patent Application Publication No. 2002-322048
Patent document 9: Japanese Unexamined Patent Application Publication No. 2002-97129
Patent document 10: Japanese Unexamined Patent Application Publication No. 2005-8596

SUMMARY OF INVENTION

Technical Problem

With high-viscosity ophthalmic compositions (especially an eye drop composition), however, the liquid drip is poor at the extraction opening (nozzle, for an eye drop composition container) during extraction from the container, and much of the liquid remains adhering to the area near the extraction opening (the outside of the nozzle, for an eye drop composition container) after the liquid has been dropped. Moreover, with an eye drop composition it is difficult in practice to conduct dropping at a constant fixed angle, and the orientation of the container varies during dropping depending on the user. The amount of residual adhesion on the nozzle tends to be especially high when the container is oriented nearly laterally (the container is parallel to the eye surface, i.e. the in-plane direction of the container is the direction perpendicular to the eye surface). This is undesirable because when an eye drop composition remain on the external surface of the nozzle after dropping, the remaining liquid can lead to contamination including adhesion of foreign matter, and as a result, the ophthalmic liquid composition can potentially be dropped through a contaminated nozzle at the time of the next use. In addition, the remaining ophthalmic liquid composition components may precipitate on the external surface of the nozzle, or the ophthalmic liquid composition may drip from the nozzle onto the container surface, thereby potentially impairing the user's perception of the product image or reliability. Furthermore, poor liquid drip from the nozzle may result in backflow of a portion of the exposed ophthalmic liquid composition or of the precipitates that have been exposed to the environment outside the container during dropping, thus increasing the risk of contamination of the ophthalmic liquid composition in the container by foreign matter. Particularly in the case of an eye drop composition, excessively poor liquid drip produces a difference in the drip volume, leading to the problem of variation in drug dosage.

It is therefore a principal object of the invention to provide a high-viscosity eye drop composition with good liquid drip at the eye drop composition container opening, and a method of improving liquid drip performance of the high-viscosity eye drop composition at the eye drop composition container opening.

Solution to Problem

The present inventors have conducted much research with the aim of solving the problems described above, and have acquired the following knowledge.

(i) An eye drop composition having a viscosity from 200 to 100,000 mPa·s, with addition of a monoterpene to a carboxyvinyl polymer, despite their high viscosity, have notably reduced liquid adhesion near the eye drop composition container opening during dropping, or in other words, the eye drop composition have improved liquid drip.

(ii) A high-viscosity eye drop composition comprising a carboxyvinyl polymer generally undergo viscosity reduction under photoirradiation, but addition of a monoterpene to the carboxyvinyl polymer to produce an eye drop composition with a viscosity from 200 to 100,000 mPa·s prevents viscosity reduction due to photoirradiation.

(iii) A high-viscosity eye drop composition cause blurred vision after dropping, but addition of a monoterpene to the carboxyvinyl polymer to produce an eye drop composition with a viscosity from 200 to 100,000 mPa·s shortens the duration of blurred vision.

The invention has been accomplished based on this knowledge, and it provides an eye drop composition, a method of improving liquid drip of an eye drop composition, a method of inhibiting viscosity reduction due to photoirradiation, and a method of improving recovery from blurred vision after ocular instillation, as described below.

1. An eye drop composition comprising a carboxyvinyl polymer and a monoterpene, and having a viscosity from 200 to 100,000 mPa·s.
2. The eye drop composition according to 1. above, wherein the monoterpene is at least one selected from the group consisting of menthol, camphor and borneol.
3. The eye drop composition according to 1. or 2. above, wherein the carboxyvinyl polymer content is from 0.001 to 10 w/v % with respect to the total volume of the eye drop composition.
4. The eye drop composition according to any one of 1. to 3. above, wherein the monoterpene content is from 0.0001 to 1 w/v % with respect to the total volume of the eye drop composition.
5. The eye drop composition according to any one of 1. to 4. above, which is filled into an eye drop composition container.
6. The eye drop composition according to 5. above, wherein the eye drop composition container is a transparent container.
7. A method of improving liquid drip performance of an eye drop composition at the eye drop composition container opening, comprising adding a monoterpene to an eye drop composition comprising a carboxyvinyl polymer to prepare an eye drop composition with a viscosity from 200 to 100,000 mPa·s.
8. A method of inhibiting viscosity reduction due to photoirradiation of an eye drop composition, comprising adding a monoterpene to an eye drop composition comprising a carboxyvinyl polymer to prepare an eye drop composition with a viscosity from 200 to 100,000 mPa·s.
9. A method of improving recovery from blurred vision after ocular instillation of an eye drop composition, comprising adding a monoterpene to an eye drop composition comprising a carboxyvinyl polymer to prepare an eye drop composition with a viscosity from 200 to 100,000 mPa·s.
10. Use of a composition comprising a carboxyvinyl polymer and a monoterpene and having a viscosity from 200 to 100,000 mPa·s, for the manufacture of an eye drop composition.
11. A composition comprising a carboxyvinyl polymer and a monoterpene and having a viscosity from 200 to 100,000 mPa·s, for use in ocular instillation.
12. A method of ocular instillation comprising a step of dropping a composition comprising a carboxyvinyl polymer and a monoterpene and having a viscosity from 200 to 100,000 mPa·s to an eye.

Advantageous Effects of Invention

With the eye drop composition of the invention, the amount of liquid remaining adhered near the eye drop composition container opening is low during dropping, i.e. the liquid drip is satisfactory, despite the high viscosity. It is therefore possible to avoid inconveniences such as deposition of the components of an eye drop composition near the container opening that results in contamination of the container, or ophthalmopathy caused by precipitated components or contaminated liquid near the container opening entering the eye. Moreover, because of the improved liquid drip, variation in the dropped liquid volume is minimized and a constant volume of liquid can be dropped in a stable manner.

An eye drop composition is usually filled into a highly transparent container for easy quality control. Generally speaking, a high-viscosity eye drop composition containing a macromolecular thickening agent exhibit reduced viscosity when exposed to light for prolonged periods, thus impairing the effects of the high-viscosity eye drop composition, such as continuous drug effect and dry-eye prevention. This tendency toward viscosity reduction is greater when a carboxyvinyl polymer is used as the macromolecular thickening agent. Since the eye drop composition of the invention have inhibited viscosity reduction by photoirradiation despite being a high-viscosity eye drop composition comprising a carboxyvinyl polymer, which tends to cause such viscosity reduction, the effects of the high-viscosity eye drop composition including continuous drug effect and dry-eye prevention are maintained even after storage.

A high-viscosity eye drop composition also usually tend to cause fogging of the field of view, also known as "blurred vision", after ocular instillation, and a prolonged state of blurred vision can create a feeling of unpleasantness. The eye drop composition of the invention, despite comprising a carboxyvinyl polymer and having high viscosity, exhibit rapid recovery from blurred vision produced after ocular instillation, and have an excellent feel during use.

Therefore, the eye drop composition of the invention is both highly safe and practical.

DESCRIPTION OF EMBODIMENTS

The present invention will now be explained in detail. The eye drop composition of the invention is an eye drop composition comprising a carboxyvinyl polymer and a monoterpene, and having a viscosity from 200 to 100,000 mPa·s.

Carboxyvinyl Polymer

The carboxyvinyl polymer (also abbreviated throughout the present specification as "CVP") is a hydrophilic polymer obtained by polymerizing acrylic acid as the major component, and it may be either polyacrylic acid or a polyacrylic acid salt.

Even when polyacrylic acid is used during admixture of each of the components, adjustment of the pH may result in a formation of polyacrylic acid salt for all or a portion of the polyacrylic acid in the composition that is obtained. Preferably, low-viscosity polyacrylic acid is used during admixture of the carboxyvinyl polymer with the other components, and the pH is adjusted so that all or a portion becomes a polyacrylic acid salt, depending on the case, to increase the viscosity of the eye drop composition. It is also preferred to use a polyacrylic acid salt from the time of mixing.

The polyacrylic acid salt used may be an alkali metal salt such as a sodium salt or potassium salt of polyacrylic acid; an amine salt such as a monoethanolamine salt, diethanolamine salt or triethanolamine salt of polyacrylic acid; or an ammonium salt of polyacrylic acid. Alkali metal salts are preferred among these.

The polyacrylic acid or its salt may be either crosslinked or non-crosslinked, but it is preferably a crosslinked polymer from the viewpoint of obtaining a high thickening effect and more prominently exhibiting the effect of the invention.

The carboxyvinyl polymer used may be a commercial product. Commercial products to be used include CARBOPOL (trade name) (Noveon, Lubrizol Corp.), SYNTHALEN (trade name), HIVISWAKO (trade name) (both by Wako Pure Chemical Industries, Ltd.), AQUPEC (trade name) (Sumitomo Seika Chemicals Co., Ltd.) and JUNRON (trade name) (Nihon Junyaku Co., Ltd.).

The carboxyvinyl polymer may be used alone or in admixture of 2 or more.

The content ratio of the carboxyvinyl polymer is not particularly restricted so long as it is the necessary content ratio so that the viscosity of the eye drop composition is within the desired range, but it is preferably about from 0.001 to 10 w/v %, more preferably about from 0.05 to 5 w/v % and even more preferably about from 0.1 to 1 w/v %, as the total amount of carboxyvinyl polymer with respect to the total volume of the eye drop composition. The desired thickening effect can be obtained if the content ratio is within this range. In addition, a content ratio within this range will produce a satisfactory effect of inhibiting viscosity reduction, a satisfactory effect of improving liquid drip and an effect of minimizing variation in drip volume, and will also produce a satisfactory feel during use.

Monoterpene

Monoterpenes include acyclic monoterpenes such as geraniol, nerol, myrcenol, linalool, linalool acetate and lavandulol; monocyclic monoterpenes such as menthol, limonene, anethole and eugenol; and bicyclic monoterpenes such as camphor, borneol, isoborneol, cineol and pinene. Of these, monocyclic monoterpenes and bicyclic monoterpenes are preferred, with menthol, camphor and borneol being more preferred. The monoterpene may be the d-form, l-form or dl-form. The monoterpene may be used alone or in combination of 2 or more.

The monoterpene may be used as an essential oil comprising it. Such essential oils include mentha oil, eucalyptus oil, peppermint oil, bergamot oil, spearmint oil and rose oil. These essential oils can be obtained from plants by known methods. Known methods for obtaining essential oils include steam distillation methods, fat or oil adsorption methods in which a plant is added to a deodorized animal fat or oil for adsorption of the essential oil and then the essential oil is extracted with ethanol, solvent extraction methods in which a plant is subjected to extraction with an organic solvent such as hexane or benzene or a supercritical fluid, the extraction solvent is dissolved in ethanol, and then the ethanol is evaporated to obtain the residue, pressing methods, and the like. The monoterpene can be recovered from the essential oil by a chromatographic method.

The monoterpene content ratio is preferably about from 0.0001 to 1 w/v %, more preferably about from 0.001 to 0.05 w/v %, even more preferably about from 0.002 to 0.05 w/v % and yet more preferably about from 0.003 to 0.02 w/v %, with respect to the total volume of eye drop composition. If the content ratio is within this range, the action of the monoterpene will be more effectively obtained, and the eye drop composition will have a good feel during use without excessive irritation.

The preferred monoterpenes are explained in detail below.

<Menthol>

A menthol that is used will usually be l-menthol or dl-menthol. The menthol used may be a commercial product, such as one by Takasago Intl. Corp., for example.

The menthol content ratio is preferably about from 0.0001 to 1 w/v %, more preferably about from 0.001 to 0.05 w/v %, even more preferably about from 0.002 to 0.05 w/v % and yet more preferably about from 0.003 to 0.02 w/v %, with respect to the total volume of the eye drop composition. If the content ratio is within this range, the action of the monoterpene will be more effectively obtained, and the eye drop composition will have a good feel during use without excessive irritation.

<Camphor>

A camphor that is used will usually be d-camphor or dl-camphor. The camphor used may be a commercial product, such as one by Takasago Intl. Corp., for example.

The camphor content ratio is preferably about from 0.0001 to 1 w/v %, more preferably about from 0.001 to 0.05 w/v %, even more preferably about from 0.002 to 0.05 w/v % and yet more preferably about from 0.003 to 0.02 w/v %, with respect to the total volume of the eye drop composition. If the content ratio is within this range, the action of the monoterpene will be more effectively obtained, and the eye drop composition will have a good feel during use without excessive irritation.

<Borneol>

A borneol that is used will usually be d-borneol or dl-borneol. The borneol used may be a commercial product, such as one by Takasago Intl. Corp., for example.

The borneol content ratio is preferably about from 0.0001 to 1 w/v %, more preferably about from 0.001 to 0.05 w/v %, even more preferably about from 0.002 to 0.05 w/v % and yet more preferably about from 0.003 to 0.02 w/v %, with respect to the total volume of the eye drop composition. If the content ratio is within this range, the action of the monoterpene will be more effectively obtained, and the eye drop composition will have a good feel during use without excessive irritation.

Boric Acid Buffer

The eye drop composition of the invention may contain a boric acid buffer. Boric acid buffers include boric acid, as well as boric acid salts such as sodium borate, potassium tetraborate, potassium metaborate, ammonium borate and borax. Preferred among these are boric acid and borax, with combinations of boric acid and borax being more preferred for use.

The boric acid buffer content ratio is preferably about from 0.05 to 3 w/v %, more preferably about from 0.2 to 2.5 w/v % and even more preferably about from 0.7 to 2 w/v %, with respect to the total volume of the eye drop composition.

Optional Components

The eye drop composition of the invention may further contain, in addition to the components mentioned above, active ingredients (pharmacologically active components or physiologically active components) that are commonly used in ophthalmic compositions. Mixing proportions for various pharmacologically active components or physiologically active components are already known in the field of eye drop composition, and the mixing proportions for pharmacologically active components or physiologically active components in the eye drop composition of the invention may be appropriately set according to the type and the like. For example, the mixing proportion of a pharmacologically active component or physiologically active component may be selected to be about from 0.0001 to 30 wt % and preferably about from 0.001 to 10 wt % with respect to the total amount of the eye drop composition.

In addition, the eye drop composition of the invention may contain various carriers or additives, either alone or in combination, by common methods depending on the purpose and form of use, so long as the effect of the invention is not impeded.

These optional components may be used alone or in combinations of 2 or more.

Viscosity

The viscosity of the eye drop composition of the invention will be usually about from 200 to 100,000 mPa·s, preferably about from 500 to 20,000 mPa·s, more preferably about from 700 to 10,000 mPa·s, even more preferably about from 1200 to 5000 mPa·s and most preferably from 1500 to 4000 mPa·s. An eye drop composition having such viscosity can be obtained mainly by appropriate selection of the type and amount of carboxyvinyl polymer used.

According to the invention, the viscosity is measured by the viscosity measuring method described in the general test method of the Japanese Pharmacopeia, 15th Edition, with a (2) simple circular cylindrical rotating viscosimeter (Brookfield viscometer). An RB-80L (Toki Sangyo Co., Ltd.) was used for the present application, and selection of the conditions including the rotor and rotational speed was according to the manufacturer's manual, with viscosity measurement at 25° C.

The simple circular cylindrical rotating viscosimeter will now be described. The simple circular cylindrical rotating viscosimeter is a viscometer that measures torque while rotating a cylinder in a liquid at a constant angular speed. The device is shown schematically in FIG. 1. A pre-calibrated standard solution for a viscometer was used to experimentally determine $K_B$, and the viscosity $\eta$ of the liquid was calculated by the following formula.

Figure 1:
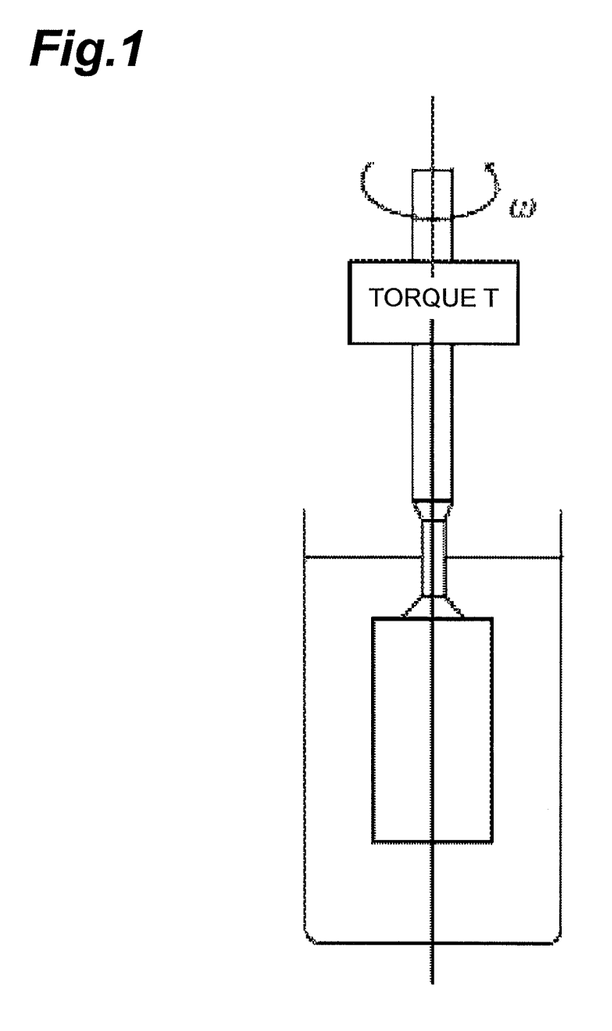
FIG. 1 is a drawing showing the general construction of a simple circular cylindrical rotating viscosimeter used for measurement of viscosity in the examples.

$\eta = K_B \times T/\omega$ $\eta$: Viscosity of liquid (mPa·s)
$K_B$: Device constant (rad/cm$^3$)
$\omega$: Angular speed (rad/s)
T: Torque acting on cylindrical surface ($10^{-7}$ N·m)

A method of measuring the viscosity of a composition expected to have a viscosity of less than about 100 mPa·s at 25° C., as with the comparative example compositions of the invention, will now be described for reference. In this case, the viscosity is measured by the viscosity measuring method described in the general test method of the Japanese Pharmacopeia, 15th Edition, with a (3) conical-flat rotating viscosimeter (cone-plate viscometer). A TV-20 (Toki Sangyo Co., Ltd.) was used for the present application, and selection of the conditions including the rotor and rotational speed was according to the manufacturer's manual, with viscosity measurement at 25° C.

The cone-plate rotating viscosimeter will now be described. The cone-plate rotating viscosimeter is a viscometer that inserts a liquid in the gap between a flat disc and a cone with a large apex angle having the same rotation axis, rotate one of them, and measures the torque and the corresponding angular speed of the other. The device is shown schematically in FIG. 2. The liquid enters the gap between the cone and flat disc at angle $\alpha$, the cone or flat disc is rotated at a constant angular speed or at a constant torque, and the torque sustained by the flat disc or cone at steady state, and the corresponding angular speed, are measured to calculate the viscosity $\eta$ of the liquid by the following formula.

Figure 2:
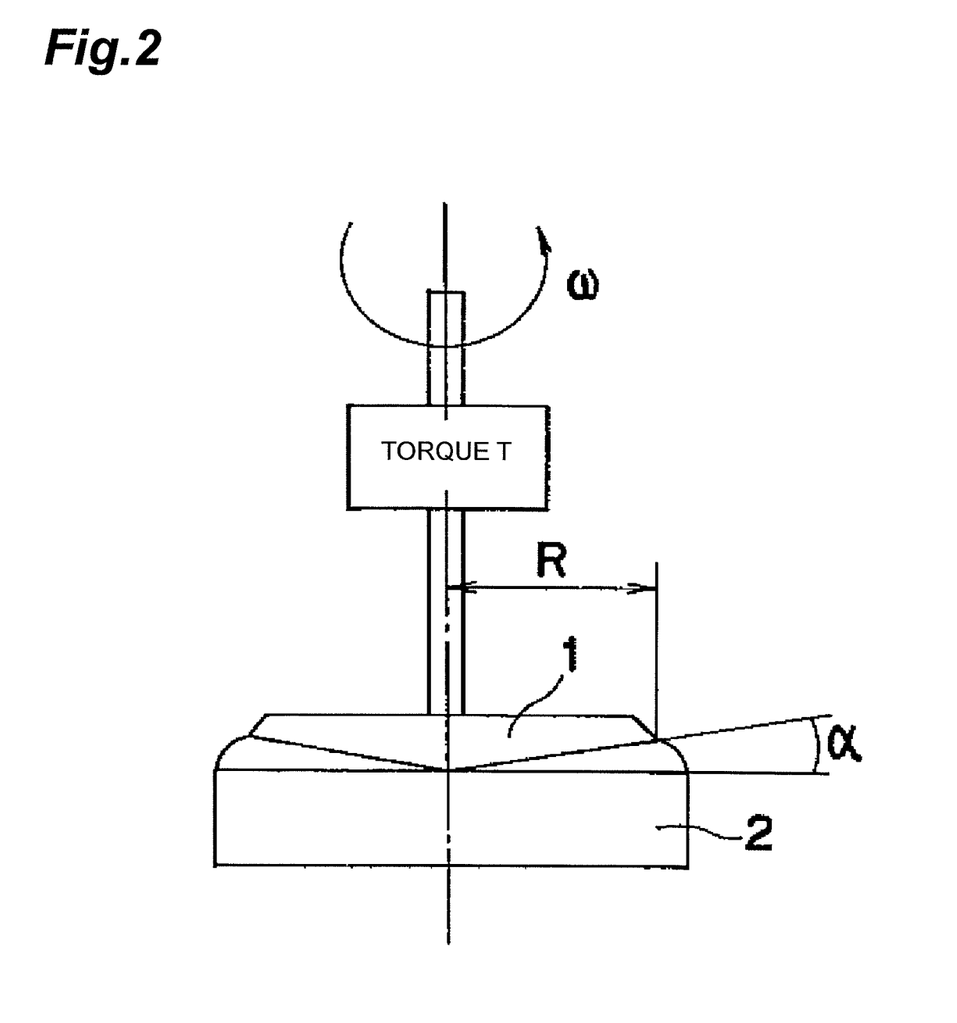
FIG. 2 is a drawing showing the general construction of a conical-flat rotating viscosimeter.

$\eta = 3\alpha/2\pi R^3 \times 100 T/\omega$ $\eta$: Viscosity of liquid (mPa·s)
$\pi$: Circular constant
R: Radius of cone (cm)
$\alpha$: Angle between flat disc and cone (rad)
$\omega$: Angular speed (rad/s)
T: Torque acting on flat disc or cone surface ($10^{-7}$ N·m)

Other Aspects

There are no particular restrictions on the dosage form of the eye drop composition of the invention. However, it is preferably a liquid drug. The pH of the eye drop composition of the invention may be about from 3 to 10, preferably about from 4 to 9, more preferably about from 5 to 8.5 and most preferably about from 7 to 8.5.

The container in which the eye drop composition of the invention are to be filled may be any known eye drop composition container without restrictions. An eye drop composition container will usually be a form which allows the eye drop composition to be dropped into the eye, such as a form comprising a nozzle with a container opening at the tip of the nozzle. The eye drop composition container holding the eye drop composition of the invention may have either a structure in which a separately formed nozzle is mounted on the container, or a structure in which the nozzle section (liquid extractor) and container body are integrally formed (for example, single-use type of an eye drop composition).

The container holding the eye drop composition of the invention may usually be made of plastic. There are no particular restrictions on the structural material of the plastic container, and examples include any one from among polyethylene terephthalate, polyallylate, polyethylene naphthalate, polycarbonate, polyethylene, polypropylene and polyimide, as well as their copolymers, or mixtures of 2 or more of the foregoing. Preferred are polyethylene terephthalate, polyallylate and polyethylene naphthalate and their copolymers and mixtures of 2 or more thereof, especially from the viewpoint of easily exhibiting the effect of the invention by adjusting the degree of extraction.

The eye drop composition of the invention may be filled into a transparent container comprising such a material as the major material (a container which is sufficiently transparent so as to not impede observation of foreign matter), or filled into a light-shielded container. The light-shielding may be accomplished, for example, by adding a coloring agent to the transparent container material, or by covering the container with a shrink film or outer casing.

The container volume is preferably about from 0.5 to 20 mL, more preferably about from 3 to 18 mL and even more preferably about from 5 to 15 mL, in order to more easily exhibit the effect of the invention by adjusting the degree of extraction.

The nozzle provided on the container holding the eye drop composition of the invention is also not particularly restricted in terms of its structure and structural materials. The nozzle structure may be any structure commonly employed for eye drop composition container nozzles, and the structural material of the nozzle may be, for example, the same structural material as the plastic container described above. From the viewpoint of further improving liquid drip of the eye drop composition of the invention and limiting variation in drip volume, the nozzle preferably comprises polyethylene or polypropylene as a structural material. The type of polyethylene may be high-density polyethylene or low-density polyethylene, but the nozzle preferably comprises low-density polyethylene as the structural material.

Production Method

The eye drop composition of the invention may be prepared by a commonly employed method or other known method (such as described in Japanese Examined Patent Application Publication No. S60-56684). For example, it may be prepared by dispersing the components (carboxyvinyl polymer, monoterpene and other optionally included pharmacologically active components or physiologically active components, and additives) in a carrier such as water, and then using a homogenizer or the like for homogenization, dissolution or emulsification, and adjusting the pH with a pH regulator.

The method of adding the monoterpene may be a method in which the monoterpene is added to an aqueous solvent, and the mixture is heated if necessary and stirred to dissolution, or a method in which the monoterpene is solubilized in a surfactant or dissolving aid added as necessary, or a polyhydric alcohol such as glycerin or propylene glycol added as necessary, and then added to an aqueous solvent. The method of sterilizing the formulation may be selected from among autoclave sterilization and filtration sterilization methods.

Application and Method of Use

The eye drop composition of the invention include an eye drop composition that may be applied while wearing contact lenses. Throughout the present specification, the term "contact lenses" includes contact lenses of various types such as hard contact lenses (including oxygen-permeable hard contact lenses) and soft contact lenses (including silicone hydrogel contact lenses).

The dosage and administration of the eye drop composition of the invention will vary depending on the symptoms and age of the patient, but may usually be administered from about 1 to 6 times per day, with from 1 to 2 drops each time.

The target of use of the eye drop composition of the invention is not particularly restricted, and may include dry eye patients (and patients with dry eye symptoms), and asthenopia patients. Particularly suitable are dry eye patients, and especially evaporative dry eye patients.

Other Modes of the Invention

By adding a monoterpene to a high-viscosity eye drop composition comprising a carboxyvinyl polymer, it is possible to improve liquid drip at the container opening during ocular instillation, while minimizing viscosity reduction. The invention therefore encompasses a method of improving liquid drip performance of an eye drop composition at the eye drop composition container opening, comprising adding a monoterpene to an eye drop composition comprising a carboxyvinyl polymer to prepare an eye drop composition with a viscosity from 200 to 100,000 mPa·s.

The invention further encompasses a method of inhibiting viscosity reduction due to photoirradiation of an eye drop composition, comprising adding a monoterpene to an eye drop composition comprising a carboxyvinyl polymer to prepare an eye drop composition with a viscosity from 200 to 100,000 mPa·s.

The invention yet further encompasses a method of improving recovery from blurred vision after ocular instillation of an eye drop composition, comprising adding a monoterpene to an eye drop composition comprising a carboxyvinyl polymer to prepare an eye drop composition with a viscosity from 200 to 100,000 mPa·s.

The invention yet further encompasses use of a composition comprising a carboxyvinyl polymer and a monoterpene and having a viscosity from 200 to 100,000 mPa·s, for the manufacture of an eye drop composition. The invention yet further encompasses a composition comprising a carboxyvinyl polymer and a monoterpene and having a viscosity from 200 to 100,000 mPa·s, for use in ocular instillation.

The invention yet further encompasses a method of ocular instillation comprising a step of dropping a composition comprising a carboxyvinyl polymer and a monoterpene and having a viscosity from 200 to 100,000 mPa·s to an eye.

The types, contents, dosage forms, viscosities, pH values, method of use and production methods for these methods are the same as for the eye drop composition described above.

EXAMPLES

The present invention will now be described in greater detail by examples, with the understanding that the invention is not limited thereto.

(1) Sample Preparation

Eye drop compositions for Examples 1 to 25 and Comparative Examples 1 to 20, the compositions of which are listed in Tables 1 to 9 below, were prepared by the following method. Specifically, a carboxyvinyl polymer or hydroxypropylmethyl cellulose was added to and dispersed in purified water while stirring, and then the other components other than the pH regulator (sodium hydroxide or hydrochloric acid) were added and the mixture was stirred for at least 1 hour to dissolution. Next, sodium hydroxide or hydrochloric acid was used to adjust the pH to from 7.3 to 7.6, and then a suitable amount of purified water was added to each formulation concentration.

Each of the prepared eye drop compositions was allowed to stand overnight in a light-shielded state at a temperature of 25° C., after which the viscosity, the osmotic pressure, the liquid adhesion on the nozzle and the viscosity reduction due to photoirradiation were measured, the variation in drip volume was evaluated, and an organoleptic evaluation was conducted.

(2) Experiment Method (2-1) Viscosity Measurement

The viscosity of each of the eye drop compositions was measured by the following method.

Examples 1 to 25, and Comparative Examples 1, 3, 4 and 7 to 20

The viscosity was measured under the following conditions using an RB-80L (Toki Sangyo Co., Ltd.), according to the test method of "(2) Simple circular cylindrical rotating viscosimeter (Brookfield viscometer)" described in the general test method in the Japanese Pharmacopeia, 15th Edition, 2nd rotating viscosimeter method for measurement of viscosity.
Measuring temperature: 25° C.
Rotational speed and rotor number
   Viscosity of more than or equal to 100 mPa·s and less than 350 mPa·s: Rotational speed: 30 rpm, Rotor No. M2
   Viscosity of more than or equal to 350 mPa·s and less than 1500 mPa·s: Rotational speed: 12 rpm, Rotor No. M2
   Viscosity of more than or equal to 1500 mPa·s: Rotational speed: 12 rpm, Rotor No. M3
Viscosity after set time of 1 minute Comparative Examples 2, 5 and 6

The viscosity was measured under the following conditions using a TV-20 (Toki Sangyo Co., Ltd.), according to the test method of "(3) conical-flat rotating viscosimeter (cone-plate viscometer)" described in the general test method in the Japanese Pharmacopeia, 15th Edition, 2nd Rotating viscosimeter method for measurement of viscosity.
Measuring temperature: 25° C.
Rotational speed of 2.5 rpm: Comparative Examples 5 and 6
Rotational speed of 100 rpm: Comparative Example 2
Rotor No. 01
Viscosity after set time of 3 minutes.

(2-2) Measurement of Viscosity Reduction Due to Photoirradiation

A 30 mL volume of each of the eye drop compositions was filled into a 30 mL-volume glass container. A Suntester (SUNTEST XLS+, product of Toyo Seiki Seisakusho, Ltd.) was used as a photoirradiation device for 8 hours of photoirradiation of the eye drop composition-filled container with an irradiance of 350 W/m². The 8 hours of photoirradiation with an irradiance of 350 W/m² corresponds to 10,000 kJ/m².

After completion of the irradiation, a sample that had not been irradiated (non-irradiated sample) and a sample that had been irradiated (irradiated sample) were stored in a light-shielded state overnight at 25° C. The viscosity at 25° C. was then immediately measured as described in "(2-1) Viscosity measurement" above.

The post-irradiation viscosity was expressed as a viscosity relative to the viscosity of the non-irradiated sample as 100%, and the viscosity reduction due to photoirradiation was evaluated for each of the eye drop compositions.

Relative viscosity (%)=[irradiated sample viscosity (25° C.)/non-irradiated sample viscosity (25° C.)]×100

(2-3) Measurement of Liquid Adhesion on Nozzle

Each of the eye drop compositions was filled into a 15 mL-volume polyethylene terephthalate eye drop composition container, and a low-density polyethylene nozzle was fitted onto the container. In consideration of the variety of situations in which an eye drop composition is used, the eye drop composition was dropped in a lateral orientation (an essentially horizontal nozzle angle), as the orientation in which liquid most readily tends to remain on the nozzle, the dropping weight per drop was measured, and the liquid adhering to the outside of the nozzle was absorbed with filter paper. This procedure was repeated 20 times, and the average drip volume was calculated. The amount of adhesion on the outside of the nozzle was measured as the total weight absorbed by the filter paper after 20 drops, and this value was divided by 20 to calculate the average weight.

(2-4) Evaluation of Variation in Drip Volume

Each of the eye drop compositions was filled into a 15 mL-volume polyethylene terephthalate eye drop composition container, and a low-density polyethylene nozzle was fitted onto the container. An eye drop composition was dropped in a lateral orientation (an essentially horizontal nozzle angle) and the dropping weight per drop was measured. This procedure was repeated 20 times, and the average drip volume (AVG), standard deviation (SD) and coefficient of variation (CV) were calculated.

(2-5) Measurement of Osmotic Pressure

The osmotic pressure of each of the eye drop compositions was measured using the osmotic pressure measuring method described in the Japanese Pharmacopeia, 15th Edition (freezing point depression method).

(2-6) Measurement of Recovery Time from Blurred Vision after Ocular Instillation of an Eye Drop Composition Three subjects were asked to drop a test eye drop composition in one eye, and to drop in the other eye, an eye drop composition with the same composition as the test eye drop composition but containing no monoterpene, and the recovery times from blurred vision after ocular instillation of both an eye drop compositions were measured.

(3) Results (3-1) Liquid Adhesion on Nozzle

Table 1 shows the compositions, pH values, osmotic pressures, viscosities, liquid adhesion amounts per drop and nozzle adhesion rates, for eye drop compositions using 1-menthol as the monoterpene.

TABLE 1

| | | | | | | (Component concentration units: g/100 ml) | |
| --- | --- | --- | --- | --- | --- | --- | --- |
| | Example 1 | Comp. Ex. 1 | Comp. Ex. 2 | Comp. Ex. 3 | Comp. Ex. 4 | Comp. Ex. 5 | Comp. Ex. 6 |
| Boric acid | 0.700 | 0.700 | 0.700 | 0.700 | 0.700 | 0.700 | 0.700 |
| Borax | 1.000 | 1.000 | 1.000 | 1.000 | 1.000 | 1.000 | 1.000 |
| 1-Menthol | 0.015 | — | 0.015 | 0.015 | — | 0.015 | — |
| Carboxyvinyl polymer (AQUPEC HV-505E) | 0.310 | 0.310 | — | — | — | 0.310 | 0.310 |
| Sodium chloride | — | — | — | — | — | 0.2 | 0.2 |
| Hydroxypropylmethyl cellulose (METOLOSE 65SH-4000) | — | — | — | 2.000 | 2.000 | — | — |
| HCl | q.s. | q.s. | q.s. | q.s. | q.s. | q.s. | q.s. |
| pH | 7.45 | 7.45 | 7.37 | 7.47 | 7.39 | 7.45 | 7.45 |
| Osmotic pressure | 216 | 212 | 282 | 265 | 259 | 275 | 283 |
| Viscosity | 2510 | 2660 | 1.01 | 1830 | 1950 | 95.0 | 91.5 |
| Liquid adhesion per drop (g) | 0.0048 | 0.0071 | 0.0008 | 0.0183 | 0.0170 | 0.0010 | 0.0001 |

In Table 1, the carboxyvinyl polymer AQUPEC HV-505E is a product of Sumitomo Seika Chemicals Co., Ltd., and the hydroxypropylmethyl cellulose METOLOSE 65SH-4000 is a product of Shin-Etsu Chemical Co., Ltd.

By comparing Example 1 and Comparative Example 1 in Table 1, it is seen that addition of menthol to the carboxyvinyl polymer can reduce adhesion on the nozzle while maintaining high viscosity. Also, comparison between Comparative Example 3 and Comparative Example 4, shows that the effect of menthol addition is an effect obtained by combination with the carboxyvinyl polymer, which is not obtained by combination with hydroxypropylmethyl cellulose even with the same thickening agent.

Since Comparative Example 2 contained no carboxyvinyl polymer and Comparative Examples 5 and 6 contained sodium chloride, they had lower viscosity than the eye drop composition of the invention. Therefore, the problem of improving liquid drip does not apply.

(3-2) Variation in Drip Volume (1)

The variations in drip volume between Example 1 and Comparative Example 1 and between Comparative Example 3 and Comparative Example 4 were compared. The variation in drip volume was calculated by an F-test (dispersion test using 2 samples, significance level: 0.05) in Microsoft Excel97. The results are shown in Table 2 below.

By comparing Example 1 and Comparative Example 1, it is seen that their P values had a significant difference in variation below the significance level, and that addition of menthol to the carboxyvinyl polymer significantly reduced the variation in drip volume. With Comparative Example 3 and Comparative Example 4 which employed hydroxypropylmethyl cellulose as the thickening agent, no significant difference in variation of drip volume was found for the P values above the significance level, and therefore clearly the effect of reducing the variation in drip volume by addition of menthol is observed in the combination with a carboxyvinyl polymer.

(3-3) Variation in Drip Volume (2)

Tables 3-6 below show the compositions, pH values, osmotic pressures, viscosities and drip volume variations (standard deviation (SD), coefficient of variation (CV)) for eye drop compositions employing 1-menthol, d-camphor or d-borneol as a monoterpene.

TABLE 3

|  | Example 2 | Example 3 | Example 4 | Comp. Ex. 7 | Example 5 | Example 6 | Example 7 | Comp. Ex. 8 |
|---|---|---|---|---|---|---|---|---|
|  |  |  |  |  |  | (Component concentration units: g/100 ml) | | |
| Boric acid | 0.7 | 0.7 | 0.7 | 0.7 | 0.7 | 0.7 | 0.7 | 0.7 |
| Borax | 1 | 1 | 1 | 1 | 1 | 1 | 1 | 1 |
| Menthol | 0.015 | — | — | — | 0.002 | 0.005 | 0.05 | — |
| d-Camphor | — | 0.02 | — | — | — | — | — | — |
| Borneol | — | — | 0.02 | — | — | — | — | — |
| CVP (CARBOPOL 980) | 0.32 | 0.32 | 0.32 | 0.32 | 0.32 | 0.32 | 0.32 | 0.32 |
| Sodium chloride | 0.06 | 0.06 | 0.06 | 0.06 | — | — | — | — |
| HCl or NaOH | q.s. | q.s. | q.s. | q.s. | q.s. | q.s. | q.s. | q.s. |
| pH | 7.40 | 7.44 | 7.44 | 7.39 | 7.43 | 7.48 | 7.47 | 7.43 |
| Osmotic pressure | 244 | 248 | 244 | 248 | 228 | 228 | 244 | 226 |
| Viscosity | 957.5 | 972.5 | 962.5 | 1020 | 2570 | 2620 | 2640 | 2640 |
| SD | 0.001591 | 0.001584 | 0.001666 | 0.004496 | 0.003806 | 0.00304 | 0.002181 | 0.004107 |
| CV (%) | 4.8 | 5.2 | 5.4 | 13.2 | 9.0 | 7.8 | 5.8 | 9.4 |

The carboxyvinyl polymer CARBOPOL 980 in Table 3 is a product of Lubrizol Corp.

TABLE 2

|  | Example 1 | Comp. Ex. 1 | Comp. Ex. 3 | Comp. Ex. 4 |
|---|---|---|---|---|
| Mean | 0.041585 | 0.057535 | 0.0694 | 0.06495 |
| Dispersion | 1.05E−05 | 2.32E−05 | 7.96E−05 | 7.49E−05 |
| Observations | 20 | 20 | 20 | 20 |
| Degree of freedom | 19 | 19 | 19 | 19 |
| Observed variance ratio | 0.454614 |  | 1.062798 |  |
| P (F ≤ f) two-tail | 0.046997 |  | 0.447889 |  |
| F Critical two-tail | 0.461201 |  | 2.16825 |  |

TABLE 4

|  | Example 8 | Comp. Ex. 9 |
|---|---|---|
|  | (Component concentration units: g/100 ml) | |
| Boric acid | 0.7 | 0.7 |
| Borax | 1 | 1 |
| Menthol | 0.015 | — |
| CVP (CARBOPOL 980) | 0.32 | 0.32 |
| Sodium chloride | 0.08 | 0.08 |
| HCl or NaOH | q.s. | q.s. |
| pH | 7.38 | 7.37 |
| Osmotic pressure | 254 | 252 |
| Viscosity | 745 | 802.5 |
| SD | 0.002782 | 0.003882 |
| CV (%) | 8.6 | 11.1 |

TABLE 5

|  | Example 9 | Example 10 | Example 11 | Example 12 | Example 13 | Comp. Ex. 10 |
|---|---|---|---|---|---|---|
|  |  |  |  |  | (Component concentration units: g/100 ml) | |
| Boric acid | 0.7 | 0.7 | 0.7 | 0.7 | 0.7 | 0.7 |
| Borax | 1 | 1 | 1 | 1 | 1 | 1 |

TABLE 5-continued

| | Example 9 | Example 10 | Example 11 | Example 12 | Example 13 | Comp. Ex. 10 |
|---|---|---|---|---|---|---|
| | | | | (Component concentration units: g/100 ml) | | |
| Menthol | 0.002 | 0.005 | 0.05 | — | — | — |
| d-Camphor | — | — | — | 0.02 | — | — |
| Borneol | — | — | — | — | 0.02 | — |
| CVP (AQUPEC HV-505E) | 0.29 | 0.29 | 0.29 | 0.29 | 0.29 | 0.29 |
| HCl or NaOH | q.s. | q.s. | q.s. | q.s. | q.s. | q.s. |
| pH | 7.43 | 7.43 | 7.42 | 7.43 | 7.42 | 7.44 |
| Osmotic pressure | 224 | 222 | 228 | 222 | 230 | 220 |
| Viscosity | 2390 | 2260 | 2360 | 2280 | 2430 | 2140 |
| SD | 0.003437 | 0.002853 | 0.002393 | 0.00257 | 0.002147 | 0.003991 |
| CV (%) | 9.3 | 7.6 | 6.2 | 6.6 | 5.4 | 10.3 |

TABLE 6

| | Example 14 | Comp. Ex. 11 | Example 15 | Comp. Ex. 12 | Example 16 | Comp. Ex. 13 |
|---|---|---|---|---|---|---|
| | | | | (Component concentration units: g/100 ml) | | |
| Boric acid | 0.7 | 0.7 | 0.7 | 0.7 | 0.7 | 0.7 |
| Borax | 1 | 1 | 1 | 1 | 1 | 1 |
| Menthol | 0.015 | — | 0.015 | — | 0.015 | — |
| CVP (AQUPEC HV-505E) | 0.31 | 0.31 | — | — | 0.31 | 0.31 |
| CVP (CARBOPOL 980) | — | — | 0.31 | 0.31 | — | — |
| Polysorbate 80 | — | — | — | — | 0.05 | 0.05 |
| HCl or NaOH | q.s. | q.s. | q.s. | q.s. | q.s. | q.s. |
| pH | 7.54 | 7.53 | 7.51 | 7.51 | 7.50 | 7.49 |
| Osmotic pressure | 210 | 228 | 214 | 220 | 222 | 236 |
| Viscosity | 1940 | 1950 | 1270 | 1255 | 1890 | 1990 |
| SD | 0.002273 | 0.003131 | 0.002243 | 0.00261 | 0.002319 | 0.002659 |
| CV (%) | 6.1 | 8.5 | 6.8 | 7.6 | 6.1 | 6.8 |

Based on Tables 3 to 6, it is seen that the eye drop compositions of the examples of the invention, which contained a monoterpene together with a carboxyvinyl polymer, had low standard deviation (SD) values and coefficient of variation (CV) values for the drip volume, and minimized variation in drip volume, compared to the eye drop compositions of the comparative examples which contained no monoterpene.

(3-4) Viscosity Reduction Due to Photoirradiation

Tables 7 to 9 below show the compositions, viscosities before and after photoirradiation, and relative viscosities, for eye drop compositions employing l-menthol, d-camphor or d-borneol as a monoterpene.

TABLE 8

| | Example 22 | Comp. Ex. 17 |
|---|---|---|
| | (Component concentration units: g/100 ml) | |
| Boric acid | 0.7 | 0.7 |
| Borax | 1 | 1 |
| Menthol | 0.015 | — |
| CVP (AQUPEC HV-505E) | 0.255 | 0.255 |
| HCl or NaOH | q.s. | q.s. |
| pH | 7.41 | 7.31 |
| Viscosity before photoirradiation (mPa·s) | 960.0 | 902.5 |

TABLE 7

| | Example 17 | Example 18 | Comp. Ex. 14 | Example 19 | Example 20 | Comp. Ex. 15 | Example 21 | Comp. Ex. 16 |
|---|---|---|---|---|---|---|---|---|
| | | | | | (Component concentration units: g/100 ml) | | | |
| Boric acid | 0.7 | 0.7 | 0.7 | 0.7 | 0.7 | 0.7 | 0.7 | 0.7 |
| Borax | 1 | 1 | 1 | 1 | 1 | 1 | 1 | 1 |
| Menthol | 0.002 | 0.05 | — | — | — | — | 0.015 | — |
| d-Camphor | — | — | — | 0.02 | — | — | — | — |
| Borneol | — | — | — | — | 0.02 | — | — | — |
| CVP (CARBOPOL 980) | 0.32 | 0.32 | 0.32 | 0.32 | 0.32 | 0.32 | 0.32 | 0.32 |
| Sodium chloride | — | — | — | 0.06 | 0.06 | 0.06 | 0.08 | 0.08 |
| HCl or NaOH | q.s. | q.s. | q.s. | q.s. | q.s. | q.s. | q.s. | q.s. |
| pH | 7.45 | 7.46 | 7.45 | 7.41 | 7.41 | 7.4 | 7.4 | 7.4 |
| Viscosity before photoirradiation (mPa·s) | 2580 | 2610 | 2560 | 950.0 | 945.0 | 955.0 | 702.5 | 752.5 |
| Viscosity after photoirradiation (mPa·s) | 592.5 | 1048 | 392.5 | 377.5 | 535.0 | 188.0 | 270.0 | 163.0 |
| Relative viscosity | 23% | 40% | 15% | 40% | 57% | 20% | 38% | 22% |

TABLE 8-continued (Component concentration units: g/100 ml)

|  | Example 22 | Comp. Ex. 17 |
|---|---|---|
| Viscosity after photoirradiation (mPa·s) | 507.5 | 138.0 |
| Relative viscosity | 53% | 15% |

TABLE 9

(Component concentration units: g/100 ml)

|  | Example 23 | Comp. Ex. 18 | Example 24 | Comp. Ex. 19 | Example 25 | Comp. Ex. 20 |
|---|---|---|---|---|---|---|
| Boric acid | 0.7 | 0.7 | 0.7 | 0.7 | 0.7 | 0.7 |
| Borax | 1 | 1 | 1 | 1 | 1 | 1 |
| Menthol | 0.015 | — | 0.015 | — | 0.015 | — |
| CVP (AQUPEC HV-505E) | — | — | 0.31 | 0.31 | 0.31 | 0.31 |
| CVP (CARBOPOL 980) | 0.31 | 0.31 | — | — | — | — |
| Polysorbate 80 | — | — | — | — | 0.05 | 0.05 |
| HCl or NaOH | q.s. | q.s. | q.s. | q.s. | q.s. | q.s. |
| pH | 7.51 | 7.51 | 7.49 | 7.48 | 7.5 | 7.49 |
| Viscosity before photoirradiation (mPa·s) | 1270 | 1255 | 1990 | 1970 | 1890 | 1990 |
| Viscosity after photoirradiation (mPa·s) | 647.5 | 437.5 | 532.5 | 193.0 | 820.0 | 522.5 |
| Relative viscosity | 51% | 35% | 27% | 10% | 43% | 26% |

From Tables 7 to 9 it is seen that the eye drop compositions of the examples of the invention, which contained a monoterpene together with a carboxyvinyl polymer, had inhibited viscosity reduction due to photoirradiation, the viscosity reduction being inhibited in a manner dependent on the monoterpene concentration, compared to the eye drop compositions of the comparative examples which contained no monoterpene.

(3-5) Recovery Time from Blurred Vision After Ocular Instillation of an Eye Drop Composition The recovery time from blurred vision after ocular instillation of an eye drop composition was measured for the eye drop composition of Example 5 (containing a carboxyvinyl polymer and menthol), having the composition shown in Table 3, and the eye drop composition of Comparative Example 8 (an eye drop composition with the same composition as Example 5 but containing no menthol). The results are shown in Table 10 below.

TABLE 10

| Subjects reported that Example 5 showed more rapid recovery from blurred vision | No difference | Subjects reported that Comp. Ex. 8 showed more rapid recovery from blurred vision |
|---|---|---|
| 3 | 0 | 0 |

From Table 10 it is seen that adding menthol together with a carboxyvinyl polymer hastens recovery from blurred vision after ocular instillation of an eye drop composition.

As mentioned above, an eye drop composition of higher viscosity usually tend to cause fogging of the field of view, or "blurred vision", after ocular instillation, and prolonged periods of blurred vision are known to cause an increased feeling of unpleasantness. The eye drop composition of Example 5 and Comparative Example 8 used in this test both had relatively high viscosities of about 2600 mPa·s.

With the eye drop composition of Comparative Example 8, which contained no menthol, the subjects reported a pasty and very poor feel during use, pooling at the lower eyelid after ocular instillation, and sticking of both eyelids when blinking, as well as a feeling of blurred vision which seemed not to subside for an extended period. On the other hand, the eye drop composition of Example 5, which further contained menthol in combination, received a high evaluation that, despite similar viscous quality as in Comparative Example 8, a sticky feel between both eyelids when blinking and blurred vision immediately after ocular instillation, these problems promptly disappeared resulting in a satisfactory field of view.

The recovery time from blurred vision after ocular instillation of an eye drop composition was evaluated for the eye drop composition of Example 9 (containing a carboxyvinyl polymer and menthol), having the composition shown in Table 5, and the eye drop composition of Comparative Example 10 (eye drop composition with the same composition as Example 9 but containing no menthol), having the composition shown in Table 5. The results are shown in Table 11 below.

TABLE 11

| Subjects reported that Example 9 showed more rapid recovery from blurred vision | No difference | Subjects reported that Comp. Ex. 10 showed more rapid recovery from blurred vision |
|---|---|---|
| 3 | 0 | 0 |

The eye drop compositions of Example 9 and Comparative Example 10 both had relatively high viscosities from about 2100 to 2400 mPa·s. Comparison between the eye drop composition of Example 9 and the eye drop composition of Comparative Example 10 also indicates that combination of menthol with a carboxyvinyl polymer hastens recovery from blurred vision after ocular instillation, and reduces unpleasant feel.

INDUSTRIAL APPLICABILITY

The eye drop composition of the invention, despite having high viscosity, exhibit satisfactory liquid drip during dropping, low variation in drip volume and minimal viscosity reduction due to photoirradiation, while also having rapid recovery from blurred vision after ocular instillation, despite the high viscosity. The eye drop composition of the invention is therefore highly practical and exhibit a satisfactory feel during use.

The invention claimed is:

1. A method of improving liquid drip performance of an eye drop composition in a transparent container at opening of a container for the eye drop composition, comprising
   mixing a monoterpene and a carboxyvinyl polymer to prepare an eye drop composition with a viscosity from 500 to 100,000 mPa·s.

2. The method according to claim 1, further comprising storing the eye drop composition in a transparent container comprising a nozzle, wherein the nozzle comprises polyethylene as a structural material.

* * * * *